(12) United States Patent
DeLuca et al.

(10) Patent No.: US 6,673,782 B2
(45) Date of Patent: *Jan. 6, 2004

(54) TREATMENT OF SYSTEMIC LUPUS ERYTHEMATOSIS

(75) Inventors: Hector F. DeLuca, Deerfield, WI (US); Margherita T. Cantorna, State College, PA (US); Jean Humpal-Winter, Poynett, WI (US)

(73) Assignee: Wisconsin Alumni Research Foundation, Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/422,571

(22) Filed: Oct. 21, 1999

(65) Prior Publication Data

US 2002/0028830 A1 Mar. 7, 2002

Related U.S. Application Data

(63) Continuation-in-part of application No. 09/301,970, filed on Apr. 29, 1999, now abandoned.

(51) Int. Cl.$^7$ ................................................ A61K 31/59

(52) U.S. Cl. ...................................... 514/167; 424/682

(58) Field of Search .......................... 514/167; 424/682

(56) References Cited

FOREIGN PATENT DOCUMENTS

WO    WO 98/14195    4/1998

OTHER PUBLICATIONS

Medline Abstract 92314302 (1992). Lemire et al.*
J.M. Lemire, et al., "1,25–Dihydroxyvitamin $D_3$ Attenuates the Expression of Experimental Murine Lupus of MRL/1 Mice," *Chemistry* 12:143–148, 1992.
J.M. Lemire, "Immunomodulatory Role of 1,25–Dihydroxyvitamin $D_3$," *J. Cell. Biochem.* 49(1) :26–31, 1992.
W.N. Roberts, "Keys to Managing Systemic Lupus Erythematosus," *Hosp. Pract.* 32(2) :113–126, 1997.
B.D. Warady, et al., "Effects of Nutritional Supplementation on Bone Mineral Status of Children with Rheumatic Diseases Receiving Corticosteroid Therapy," *J. Rheum.* 21(3):530–535, 1994.
J. Abe, et al., "Prevention of Immunological Disorders in MRL/1 Mice by a New Synthetic Analogue of Vitamin $D_3$:22–Oxa–1α, 25–Dihydroxyvitamin $D_3$," *J. Nutr. Sci. Vitaminol.* 36:21–31, 1990.
C.H. Basel, "Wissenshaftliche Tabellen" *Documenta Geigy*, p. 490, 1968.
L. Binderup, "Immunological Properties of Vitamin D Analogues and Metabolites," *Biochem. Pharma.* 43(9):1885–1892, 1992.
J.E. Garcia Diaz, et al., "Evolution of the Bone Mass (BM) in Therapy with Calcium: Vitamin D and Etidronate (C+V+E) in Patients (P) with Lupus Nephritis (LN) and Chronic Glucocorticoid Treatment (CGT)," *Neph. Dial. Trans.* 10(6):964, 1995.
A.V. Kukhtevich, et al., "Treatment of Bone Disorders in Renal Diseases," *Biosci. Inform. Serv.* 71(8) :59–62, 1999 (Abstract).

* cited by examiner

*Primary Examiner*—Zohreh Fay
(74) *Attorney, Agent, or Firm*—Quarles & Brady LLP

(57) ABSTRACT

A method of treating SLE symptoms of an SLE patient comprising administering to an SLE patient an amount of vitamin D compound effective to reduce symptoms and observing a reduction in symptoms is disclosed.

10 Claims, 3 Drawing Sheets

(The drop in the severity score of the control group at 19 weeks of age was due to the death of several animals with severe scores.)

TREATMENT OF SYSTEMIC LUPUS ERYTHEMATOSIS

CROSS-REFERENCE TO RELATED APPLICATION

This application is a continuation-in-part of U.S. Ser. No. 09/301,970, filed Apr. 29, 1999, now abandoned, which is incorporated by reference as if fully set forth below.

STATEMENT REGARDING FEDERALLY SPONSORED RESEARCH OR DEVELOPMENT

BACKGROUND OF THE INVENTION

Systemic lupus erythematosis (SLE) is a systemic autoimmune disease with the potential to be directly involved in multiple organ systems. (See review by Kotzin, B. L., *Cell* 85:303–306, 1996.) The clinical manifestations of SLE include skin rash and joint pain, and severe and progressive kidney involvement. SLE patients typically present elevated serum levels of antibodies to nuclear constituents (i.e., antinuclear antibodies). In order to study the disease, workers have employed several animal models, including the F1 hybrid of New Zealand Black (NZB) and New Zealand White (NZW) mice, MRL mice homozygous for the lymphoproliferation (lpr) gene and BXSB mice, which carry the disease accelerating Yaa gene on the Y chromosome.

Principal targets of the autoantibodies produced in SLE patients include protein-nucleic acid complexes, such as chromatin, the U1 and Sm small nuclear ribonucleoprotein (snRNP) particles and the Ro/SSA and La/SSB RNP complexes (Tan, 1989; Cotson and Odell, 1995). Autoantibodies to phospholipids and cell surface molecules are also detected.

A majority of patients with SLE have symptoms of kidney failure. Clinical presentations typically include asymptomatic hematuria or proteinuria, acute nephritic or nephrotic syndromes, rapidly progressive glomerulonephritis and chronic renal insufficiency. (See Austin and Balow, *Seminars in Nephrology* 19(1):2–11, 1999.)

Current treatments have addressed lupus nephritis, although commonly used therapeutic regimes are potentially toxic and may be ineffective for some high risk patients. Typically, intensive immunosuppressive regimes are prescribed. For severe SLE, immunosuppressives such as chemotherapies and cyclosporin are used. Other treatments include treatment with corticosteroids and cytotoxic drugs. Alternative therapies include treatment with cyclophosphamide and prednisone. Side effects of long term use of prednisone include development of high blood pressure, diabetes and osteoporosis.

Currently, many pharmaceutical companies are searching for alternative therapies. La Jolla Pharmaceutical Company (La Jolla, Calif.) is conducting phase II/III trials of LJP394 Toleragen, designed to target B cells that display anti-double stranded DNA antibodies that are implicated in kidney damage. Genelabs Technologies, Inc. is conducting a phase III trial of DHEA, a naturally occurring androgen, with the goal of overall disease reduction. Other drug therapies include IDEC-131, a humanized monoclonal antibody that targets CD40 on helper T cells (Idec Pharmaceuticals Corp., San Diego, Calif.) and a 5G1.1 C5 complement inhibitor (Alexion Pharmaceuticals, New Haven, Conn.).

Lemire, et al., *Autoimmunity* 12(2):143–148, 1992, describes the attenuation by 1,25-dihydroxyvitamin $D_3$ of some symptoms of experimental murine lupus in MRL/I mice.

$1,25(OH)_2D_3$ and Analogs

The 1α-hydroxylated metabolites of vitamin D—most importantly 1α,25-dihydroxyvitamin $D_3$ and 1α,25-dihydroxyvitamin $D_2$—are known as highly potent regulators of calcium homeostasis in animals and humans. More recently, their activity in cellular differentiation has also been established. As a consequence, many structural analogs of these metabolites, such as compounds with different side-chain structures, different hydroxylation patterns, or different stereochemistry, have been prepared and tested. Important examples of such analogs are 1α-hydroxyvitamin $D_3$, 1α-hydroxyvitamin $D_2$, various side-chain fluorinated derivatives of 1α,25-dihydroxyvitamin $D_3$, and side-chain homologated analogs. Several of these known compounds exhibit highly potent activity in vivo or in vitro, and possess advantageous activity profiles and thus are in use, or have been proposed for use, in the treatment of a variety of diseases such as renal osteodystrophy, vitamin D-resistant rickets, osteoporosis, psoriasis, multiple sclerosis, arthritis and certain malignancies.

1,25-Dihydroxyvitamin $D_3$ as an Immunomodulator

The first indication that vitamin D might modulate immunity was the discovery that peripheral blood monocytes and activated T lymphocytes have 1,25-dihydroxyvitamin $D_3$ receptors (reviewed in Manolagas, S. C., et al., *Mol. and Cell. Endocrin.* 43:113–122, 1985). Despite many investigations, 1,25-dihydroxyvitamin $D_3$ immunomodulatory activity remains largely undefined and often controversial (reviewed in Manolagas, S. C., et al., supra, 1985; Rigby, W. F. C., *Today* 9:54–57, 1988; and Lemire, J. M., et al., *J. Nutr.* 125:1704S-1708S, 1995).

The action of 1,25-dihydroxyvitamin $D_3$ on human peripheral blood mononuclear cells (PBMC) has been studied extensively in vitro. These in vitro experiments showed that the hormone inhibited mitogen-stimulated proliferation of the PBMC (Lemire, J. M., et al., *J. Clin. Invest.* 74:657–661, 1984; Rigby, W. F. C., et al., *J. Clin. Invest.* 74:1451–1455, 1984) by reducing IL-2 production (Lemire, J. M., et al., *J. Immunol.* 134:3032, 1985; Iho, S., et al., *Immunol. Let.* 11:331–336, 1985; Manolagas, S. C., et al., *J. Clin. Endocrinol. Met.* 63:394, 1986) at the level of gene transcription (Alroy, I., et al., *Mol. Cell. Biol.* 15:5789–5799, 1995). In contrast, Bhalla, et al. (Bhalla, A. K., et al., *J. Immunol.* 133:1748–54, 1984) reported that the hormone did not inhibit mitogen-stimulated mouse spleen and thymus cell proliferation, although it did inhibit antigen-stimulated proliferation of these cells. Lacey, et al. (Lacey, D. L., et al., *J. Immunol.* 138:1680–1686, 1987) reported that the hormone actually stimulated mitogen-induced proliferation of cloned mouse T-cells. No studies have directly addressed the action of the hormone on T lymphocyte differentiation and function in vivo.

Disparate results have been reported for T lymphocyte IFN-γ synthesis in vitro. Rigby, et al. (Rigby, W. F. C., et al., *J. Clin. Invest.* 79:1659–1664, 1987) and Reichel, et al. (Reichel, H., et al., *Proc. Natl. Acad. Sci. USA* 84:3387–3389, 1987) showed that 1,25-dihydroxyvitamin $D_3$ decreased IFN-γ synthesis in mitogen-stimulated PBMC. However, Muller, et al. (Muller, K., et al., *Immunol. Let.* 35:177–182, 1993) reported that the hormone had no effect on IFN-γ synthesis in human T-cell lines. The hormone inhibited cytotoxic T lymphocyte development but not cytotoxic function (Merino, F., et al., *Cell. Immunol.* 118:328–336, 1989).

There is controversy about 1,25-dihydroxyvitamin $D_3$ action on monocyte/macrophage cells in vitro. 1,25-

Dihydroxyvitamin $D_3$ enhanced a myeloid leukemia cell's differentiation to the macrophage phenotype (Manologas, S. C., et al., supra, 1985). It also increased monocyte/macrophage production of M-CSF, TNF-α, and prostaglandin E2, but decreased IL-12 synthesis (Lemire, J. M., et al., *FASEB J.* 8:A745 (abs), 1994). The hormone decreased macrophage costimulatory function for T-cell proliferation (Rigby, W. F. C. and M. G. Waugh, *Arthritis Rheum.* 35:110–119, 1992). Disparate results have been reported for 1,25-dihydroxyvitamin $D_3$ effects on IL-1 synthesis in vitro. The hormone decreased IL-1 synthesis in some reports (Iho, S., et al., supra, 1985; Tsoukas, C. S., et al., *J. Clin. Endocrinol. Metab.* 69:127–133, 1989) and increased IL-1 synthesis in other reports (Amento, E. P., *J. Clin. Invest.* 73:731–739, 1987; Bhalla, A. K., et al., *Immunol.* 72:61–64, 1991; Fagan, D. L., et al., *Mol. Endocrinol.* 5:179–186, 1991). Likewise, some investigators reported that 1,25-dihydroxyvitamin $D_3$ enhanced class II protein expression in vitro (Morel, P. A., et al., *J. Immunol.* 136:2181–2186, 1986) but others reported that it decreased class II protein expression (Amento, E. P., supra, 1987; Carrington, M. N., et al., *J. Immunol.* 140:4013–4018, 1988; Rigby, W. F. C., et al., *Blood* 76:189–197, 1990). Together these findings provide no clear and consistent view of how 1,25-dihydroxyvitamin $D_3$ might modify macrophage function. No studies have directly addressed the action of the hormone on monocyte/macrophage differentiation and function in vivo.

There is also controversy about 1,25-dihydroxyvitamin $D_3$ action on B lymphocytes (reviewed in Rigby, W. F. C., supra, 1988). Lemire, et al. (Lemire, J. M., et al., supra, 1984) reported that the hormone inhibited mitogen-stimulated $I_gG$ and $I_gM$ synthesis by human peripheral blood mononuclear cells. Suppressive and enhancing effects of 1,25-dihydroxyvitamin $D_3$ on mitogen-stimulated B cell proliferation and on antibody synthesis in vitro have been shown. In vivo, 1,25-dihydroxyvitamin $D_3$ has been reported to enhance antibody synthesis in some studies (Abe, J., et al., *Endocrinology* 124:2645–2647, 1989; Ross, T. K., et al., *Vitamins Hormones* 49:281–326, 1994; Daynes, R. A., et al., *Infec. Immun.* 64:1100–1109, 1996) and to inhibit it in other studies (Lemire, J. M., et al., supra, 1995).

BRIEF SUMMARY OF THE INVENTION

The present invention is a method of preventing SLE symptoms in susceptible individuals and SLE patients by administering an amount of a vitamin D compound, preferably $1,25(OH)_2D_3$ or analogs thereof, effective to prevent SLE symptom development or to diminish the SLE symptoms, respectively. (By "SLE symptoms" applicants refer to the lymph node swelling and proteinuria that are characteristic of SLE.) The method comprises selecting an SLE patient and administering a sufficient amount of the vitamin D analog to the patient such that the SLE symptoms are abated. Preferably, the patient will show a reduction in proteinurea levels to less than 100 mg/dL. Preferably, the patient will also be on a calcium-containing diet wherein the patient's calcium intake is at least 800 mg/day/160 lb patient of calcium. A preferred range is 800 mg/day–1.5 g/day/160 lb patient.

In a particularly advantageous form of the reaction, the administered compound is either 1α,25-dihydroxyvitamin $D_3$ (1, 25-$(OH)_2D_3$), 19-nor-1,25-dihydroxyvitamin $D_2$ (19-nor-1,25-$(OH)_2D_3$), 24-homo-22-dehydro-22E-1α,25-dihydroxyvitamin $D_3$ (24-homo-22-dehydro-22E-1,25-$(OH)_2D_3$), 1,25-dihydroxy-24(E)-dehydro-24-homo-vitamin $D_3$ (1,25-$(OH)_2$-24-homo $D_3$), or 19-nor-1,25-dihydroxy-21-epi-vitamin $D_3$ (19-nor-1,25-$(OH)_2$-21-epi-$D_3$). In a most preferred form of the invention, the compound is $1,25(OH)_2D_3$.

A preferred dose of vitamin D compound for the present invention is the maximum that a patient can tolerate and not develop hypercalcemia.

If the vitamin D compound is not a 1α-hydroxy compound, a particularly advantageous daily dose of vitamin D compound is between 5.0 and 50 μg per day per 160 pound patient. If the vitamin D compound is a 1α-hydroxy compound, the preferred dose is between 0.5 and 25 μg per day per 160 pound patient. In this embodiment of the invention, the amount of $1,25(OH)_2D_3$ administered could be as high as 1.5 μg per day per 160 pound patient. A preferred dose would be 0.5–5 μg per day per 160 pound patient.

It is an advantage of the present invention that the method diminishes the SLE symptoms of proteinuria and lymph node swelling.

It is another advantage of the present invention that the method diminishes SLE symptom onset.

It is another advantage of the present invention that the method that the vitamin D compound is administered orally.

It is another advantage of the present invention that susceptible individuals can be prophylactically treated to prevent the development of SLE.

It is another advantage of the present invention that bone loss does not occur as a side effect of treatment.

Other advantages and features of the present invention will become apparent after examination of the specification, claims and drawings.

DETAILED DESCRIPTION OF THE INVENTION

Figure 1:
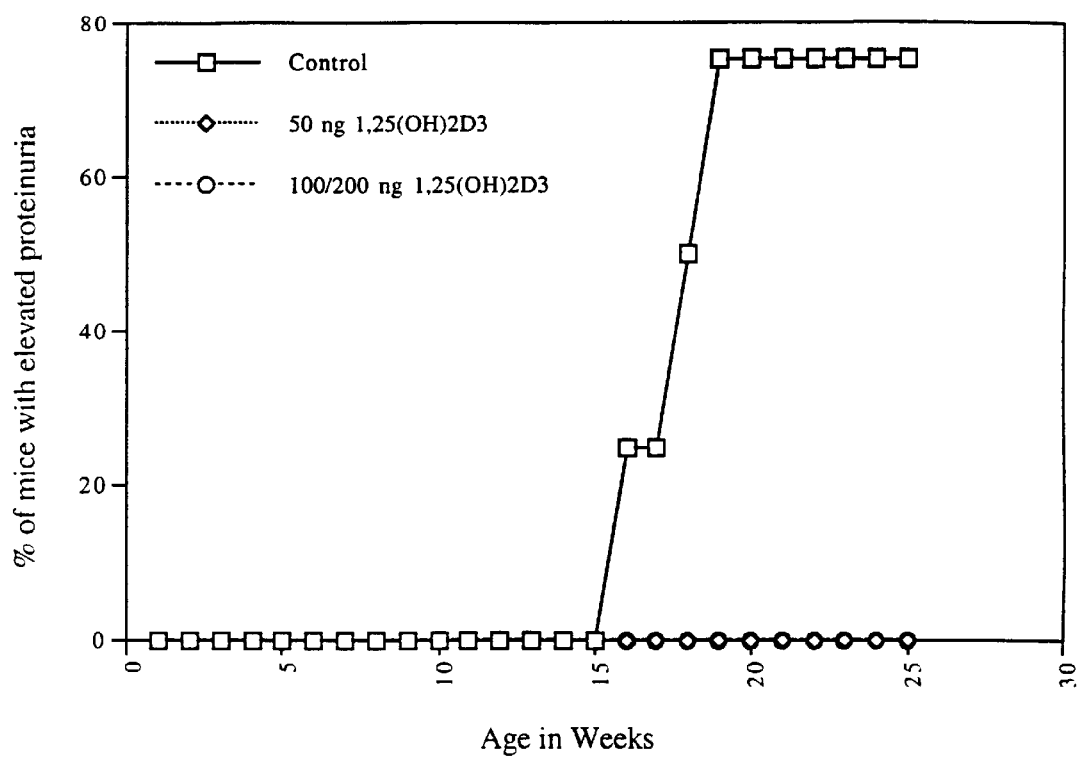
FIG. 1 is a graph of proteinuria severity in control and $1,25(OH)_2D_3$-treated MRL/MPJ mice versus mouse age.

The present invention is a method of treating human SLE patients by administering an amount of a vitamin D compound, preferably $1,25(OH)_2D_3$ or analogs thereof, effective to diminish specific SLE symptoms. The method comprises selecting an SLE patient and administering a sufficient amount of the vitamin D analog to the patient such that the SLE symptoms are abated. In the preferred embodiment of the invention, the patient has an adjusted calcium intake of at least 800 mg/day/160 lb patient.

In a particularly advantageous form of the reaction, the administered compound is either 1α,25-dihydroxyvitamin $D_3$ (1,25-$(OH)_2D_3$), 19-nor-1,25-dihydroxyvitamin $D_2$ (19-nor-1,25-$(OH)_2D_3$), 24-homo-22-dehydro-22E-1α,25-dihydroxyvitamin $D_3$ (24-homo-22-dehydro-22E-1,25-$(OH)_2D_3$), 1,25-dihydroxy-24(E)-dehydro-24-homo-vitamin $D_3$ (1,25-$(OH)_2$-24-homo $D_3$), or 19-nor-1,25-dihydroxy-21-epi-vitamin $D_3$ (19-nor-1,25-$(OH)_2$-21-epi-$D_3$)

In another form of the present invention, the vitamin D compound has the formula

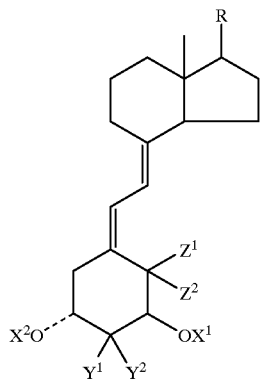

wherein $X^1$ and $X^2$ are each selected from the group consisting of hydrogen and acyl; wherein $Y^1$ and $Y^2$ can be H, or one can be 0-aryl, 0-alkyl, aryl, alkyl of 1-4 carbons, taken together to form an alkene having the structure of

where $B_1$ and $B_2$ can be selected from the group consisting of H, alkyl of 1-4 carbons and aryl, and can have a β or α configuration; $Z^1=Z^2=H$ or $Z^1$ and $Z^2$ together are $=CH_2$; and wherein R is an alkyl, hydroxyalkyl or fluoroalkyl group, or R may represent the following side chain:

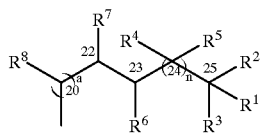

wherein (a) may have an S or R configuration, $R^1$ represents hydrogen, hydroxy or O-acyl, $R^2$ and $R^3$ are each selected from the group consisting of alkyl, hydroxyalkyl and fluoralkyl, or, when taken together represent the group-$(CH_2)_m$-wherein m is an integer having a value of from 2 to 5, $R^4$ is selected from the group consisting of hydrogen, hydroxy, fluorine, O-acyl, alkyl, hydroxyalkyl and fluoralkyl, wherein if $R^5$ is hydroxyl or fluoro, $R^4$ must be hydrogen or alkyl, $R^5$ is selected from the group consisting of hydrogen, hydroxy, fluorine, alkyl, hydroxyalkyl and fluoralkyl, or $R^4$ and $R^5$ taken together represent double-bonded oxygen, $R^6$ and $R^7$ taken together form a carbon—carbon double bond, $R^8$ may be H or $CH_3$, and wherein n is an integer having a value of from 1 to 5, and wherein the carbon at any one of positions 20, 22, or 23 in the side chain may be replaced by an O, S, or N atom.

One may evaluate a candidate vitamin D compound for its suitability for the present invention. The candidate compound should first be subjected to an initial mouse-model screening procedure, such as that described below for 1,25-$(OH)_2D_3$ in the Examples below. A successful compound will reduce the SLE symptoms of lymph node swelling and proteinuria in MRL/MPJ mice, preferably to the extent shown in the Examples for 1,25-$(OH)_2D_3$. However, a successful compound is generally described as one that reduces SLE symptoms.

Preferably, the compound should show a significant reduction in proteinuria. Preferably, the treated mouse will show a reduction in proteinurea levels to less than 100 mg/dL. Preferably, the proteinuria percentage in treated mice will be less than 50% that of control. Most preferably, the proteinuria level will be less than 10% that of control. The compound would then be predicted to be successful in human patients.

A preferred dose of vitamin D compound for the present invention is the maximum that a patient can tolerate and not develop hypercalcemia.

If the vitamin D compound is not a 1a-hydroxy compound, a particularly advantageous daily dose of vitamin D compound is between 5.0 and 50 μg per day per 160 pound patient.

If the vitamin D compound is a 1α-hydroxy compound, the preferred dose is between 0.5 and 25 μg per day per 160 pound patient. In this embodiment of the invention, the amount of 1,25$(OH)_2D_3$ administered could be as high as 1.5 μg per day per 160 pound patient. A preferred dose would be 0.5–1.5 μg per day per 160 pound patient.

1,25-dihydroxyvitamin $D_3$ (1,25-$(OH)_2D_3$) is currently administered at a level of 0.5 μg/day per 160 pound patient, usually in two quarter microgram capsules morning and night for the treatment of osteoporosis or renal osteodystrophy. Dietary calcium should be on the order of 800 mg–1.5 g/day. Our results below in the Examples indicate that treatment with 1,25$(OH)_2D_3$ is not effective when used with low calcium diets (under 500 mg/day per 160 patient).

Therefore, the maximum preferred dose of 1,25-$(OH)_2D_3$ would appear to be at 0.5–0.75 μg/day. Other less active 1α-hydroxy vitamin D compounds can be given at higher doses safely. For example, in Japan the treatment of osteoporosis with 1,25-$(OH)_2D_3$ is 0.5 to 1.0 μg/day. The same is true of other countries, such as Italy, where as much as 1 μg/day of 1,25-$(OH)_2D_3$ has been successfully used by Dr. Caniggia (Caniggia, A., et al., *Metabolism* 39:43–49, 1990).

We also envision a lower preventative dose of vitamin D compound in susceptible people.

We believe that for the treatment of existing SLE disease, higher dose of 1,25-$(OH)_2D_3$ would be most helpful.

A preferred treatment regime would be the following: Increase the patient's calcium intake to at least 800 mg/day, possibly by calcium supplements and increasing the consumption of dairy products. Under these circumstances, the dose of 1,25-$(OH)_2D_3$ can be safely increased to up to 1.5 μg if given at night.

A preferred mode of treatment is daily, oral administration, preferably with a slow release formulation or a slow release compound. Applicants specifically envision that a fairly continuous dosing of vitamin D compound is advantageous in reduction of SLE disease symptoms.

The preferred mode of treatment for 1a-hydroxy compounds is administration of 0.5–0.75 μg/day of the compound. A preferred method would be to administer 0.75–1 μg/day at 10 p.m. or before bedtime. A most preferred method would be to both increase the dietary calcium intake to at least 800 mg/day and to administer between 0.75 and 1.5 μg/day of the compound at 10 p.m.

A preferred mode of treatment for non-1α-hydroxy compounds would also be administration under dietary circumstances in which the patient receives at least 800 mg/day calcium. In this case, the treatment dose could be increased up to 50 μg/day per 160 pound patient.

An optimum treatment dose will be determined upon observation of reduction of the patient's symptoms as a function of the amount of vitamin D compound administered.

By "SLE symptoms" we mean disease symptoms characterized by elevated proteinuria levels and lymph node swelling.

By a "reduction in SLE symptoms" we mean that the patient's proteinuria level will be less than 50% that of untreated SLE patients. Preferably, the proteinuria level will be less than 10% that of untreated SLE patients.

The method of the present invention is also useful for delaying or preventing the onset of SLE in susceptible individuals.

SLE is a multigenetic disease and little is known about which genes control susceptibility to this disease. What is known is that first degree relatives (children, parents, siblings) have a 5% risk of developing SLE compared to only a 0.001% in the general public. If one twin has SLE, the other has a 11–69% chance of getting the disease. We envision that first degree relatives of SLE patients are a likely pool of susceptible individuals who would benefit from prophylactic treatment. Future screening with genetic markers as they become available will allow one to determine other susceptible individuals. Additionally, it is known that more than 85% of SLE patients are female. See Cooper, *Arthritis and Rheumatism* 41(10):1714–1724, 1998.

The experiments below demonstrate a reduction or elimination of SLE symptoms in model mice. We predict a similar type of reduction of symptoms in human patients.

It is an advantage of the present invention that bone loss does not occur as a side effect as in other treatments. For example, see Trapani, S., et al., *Rheumatol. Int.* 18:45–49, 1988 and Kipen, Y., et al., *J. Rheumatol.* 26:310–317, 1999.

EXAMPLES

The experimental evidence presented below demonstrates that $1,25(OH)_2D_3$ prevented or slowed SLE symptoms in mice on a 0.87% calcium diet but did not inhibit these symptoms in mice on a 0.02% calcium diet.

A. 0.87% Calcium Diet

MRL mice are the model for the human disease lupus. See Brians, et al., *J. Exp. Med.* 148:1198–1215, 1978 and P. L. Cohen and R. A. Eisenburg, *Annu. Rev. Immunol.* 9:243–69, 1991.

When the MRL mice in this study were 4 weeks old, they were started on one of three experimental diets. All mice were fed the experimental diet which contains 0.87% Ca. Control mice are fed the experimental diet with no $1,25 (OH)_2D_3$; one group of 7 mice were fed the experimental diet with 50 ng/mouse/day of $1,25(OH)_2D_3$; and another group of 8 mice were fed the experimental diet with 200 ng/mouse/day of $1,25(OH)_2D_3$. The mice were checked weekly for physical symptoms. In control-fed MRL mice, SLE disease symptoms spontaneously develop after 5 weeks. Symptoms were given numbers from 0.5 to 3, with 0.5 being small sores; 1, swollen lymph nodes under front legs; 2, swollen lymph nodes under front legs and on neck; 3, swollen lymph nodes under front legs, neck and back legs (severity scores for table).

Proteinuria levels were checked weekly started at 16 weeks of age.

At 10 weeks of age the 200 ng $1,25-(OH)_2D_3$ dosed animals began to show symptoms of hypercalcemia. The diet was then replaced with the same diet providing a dose level of 100 ng/mouse/day.

Figure 2:
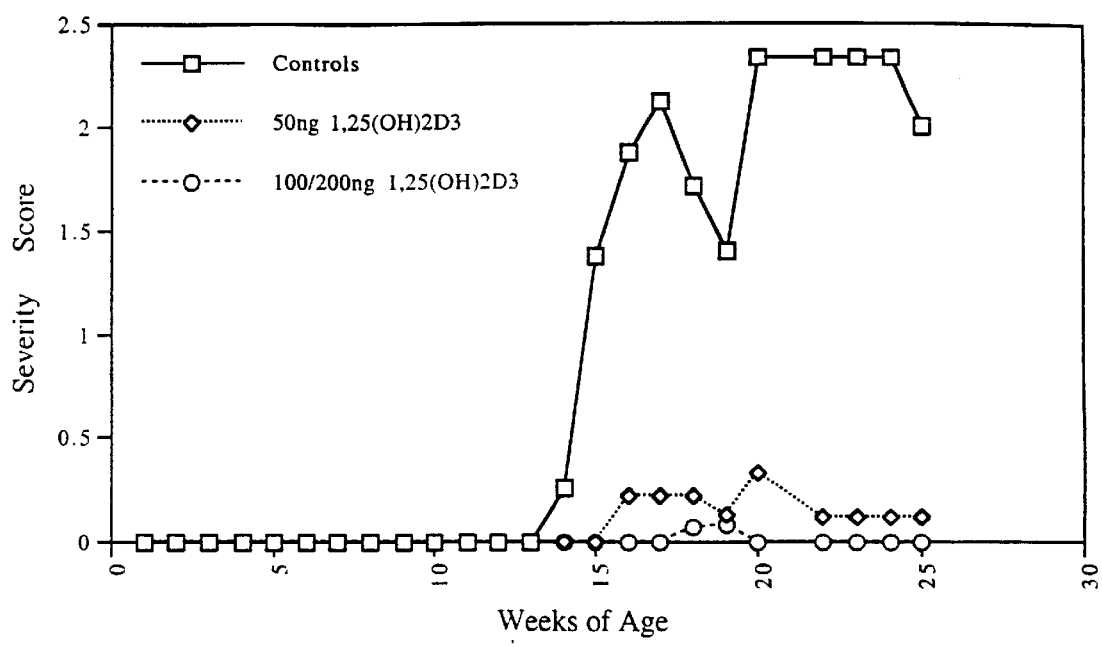
FIG. 2 is a graph of SLE severity of control and $1,25$-$(OH)_2D_3$-treated MRL/MPJ mice versus age in mouse.

The first physical symptoms of lupus began to develop in two female control-fed mice at 14 weeks of age. None of the $1,25(OH)_2D_3$-treated mice showed symptoms at this time. At 17 weeks of age the control mice started to die. Their proteinuria levels were elevated above 300 mg/dl. (Normal proteinuria levels are 30 mg/dL or lower.) At this time, the 1,25 treated animal began to die of what we believe to be hypercalcemia. FIGS. 1 and 2 demonstrates the results of these experiments. FIG. 1 compares the percentage of mice with elevated proteinuria with the age of the mouse. FIG. 2 compares the severity of the SLE with symptoms the age of the mice.

Serum calcium values were measured and found to be at 8 mg %Ca for the controls, and 12 mg %Ca for both the 50 ng and 100 ng treated groups. The $1,25(OH)_2D_3$ treatment diet was removed at 17 weeks of age, and all mice were fed the 0.87% calcium control diet for the remainder of the experiment. The results of the above-described experiment are tabulated in Table 1 and Table 2 below. Table 1 indicates that none of the $1,25(OH)_2D_3$ treated mice developed proteinuria of 100 mg/dL or greater. Table 2 indicates that the disease severity scores were much less for the treated mice than for controls.

TABLE 1

% of Mice with Proteinuria at 100 mg/dL and Greater

| Age in weeks | Control | 50 ng 1.25 | 100/200 ng 1.25 |
| --- | --- | --- | --- |
| 0–15 | 0% | 0% | 0% |
| 16–17 | 25% | 0% | 0% |
| 18 | 50% | 0% | 0% |
| 19–25 | 75% | 0% | 0% |

TABLE 2

Severity of MRL/MPJ Scores

Mean scores of disease severity

| Age in weeks | Controls | 50 ng 1.25 | 100/200 ng 1.25 |
| --- | --- | --- | --- |
| 0–13 | 0.00 | 0.00 | 0.00 |
| 14 | 0.25 | 0.00 | 0.00 |
| 15 | 1.37 | 0.00 | 0.00 |
| 16 | 1.87 | 0.21 | 0.00 |
| 17 | 2.12 | 0.21 | 0.00 |
| 18 | 1.71 | 0.21 | 0.07 |
| 19 | 1.4 | 0.12 | 0.08 |
| 20 | 2.33 | 0.33 | 0.00 |
| 21 | 2.33 | 0.11 | 0.00 |
| 22 | 2.33 | 0.11 | 0.00 |
| 23 | 2.33 | 0.11 | 0.00 |
| 24 | 2.00 | 0.11 | 0.00 |

B. 0.02% Calcium Diet Group

MRL/MPJ-Fas<lpr>mice were raised on a chow diet. At 5–6 weeks of age 13 mice were switched to a purified diet containing 0.02% calcium and 14 mice were put on a diet containing 0.02% calcium with 100 ng of $1,25(OH)_2D_3$ per/mouse/day. The mice were checked weekly for physical symptoms of lupus. The symptoms were given numerical scores starting at 0.5=small sore on skin; 1=swollen lymph nodes under front legs; 2=swollen lymph nodes under front legs and neck; 3=swollen lymph nodes under front legs, neck, and back legs (severity scores used in figure on the next page).

Figure 3A:
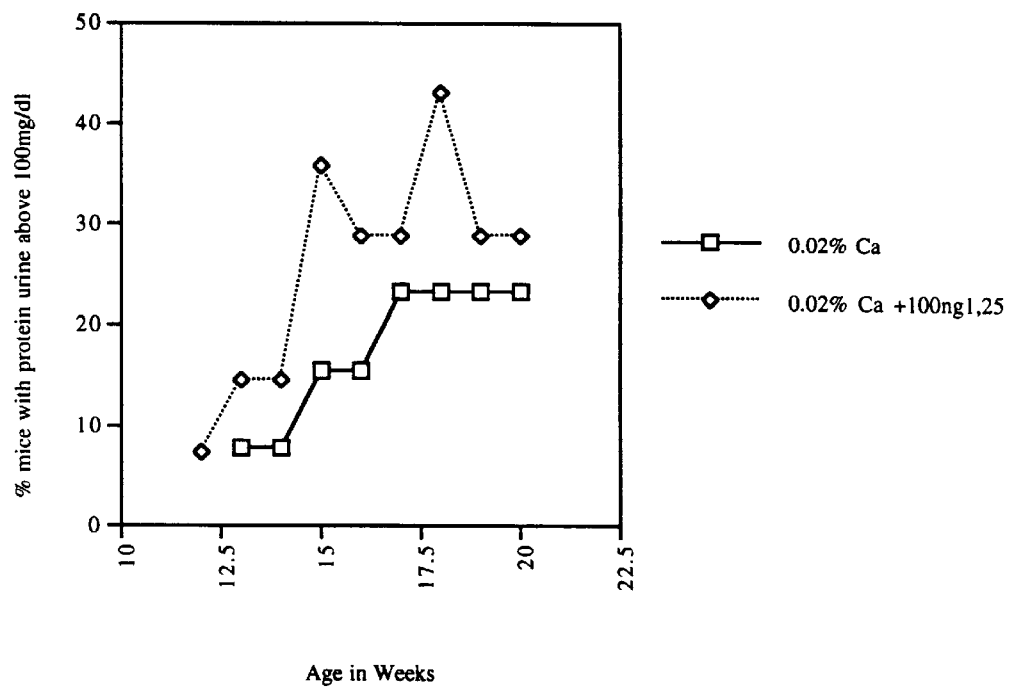
FIGS. 3A and B are graphs of proteinuria (FIG. 3A) and mean symptom score (FIG. 3B) in mice on a 0.02% calcium diet.
Figure 3B:
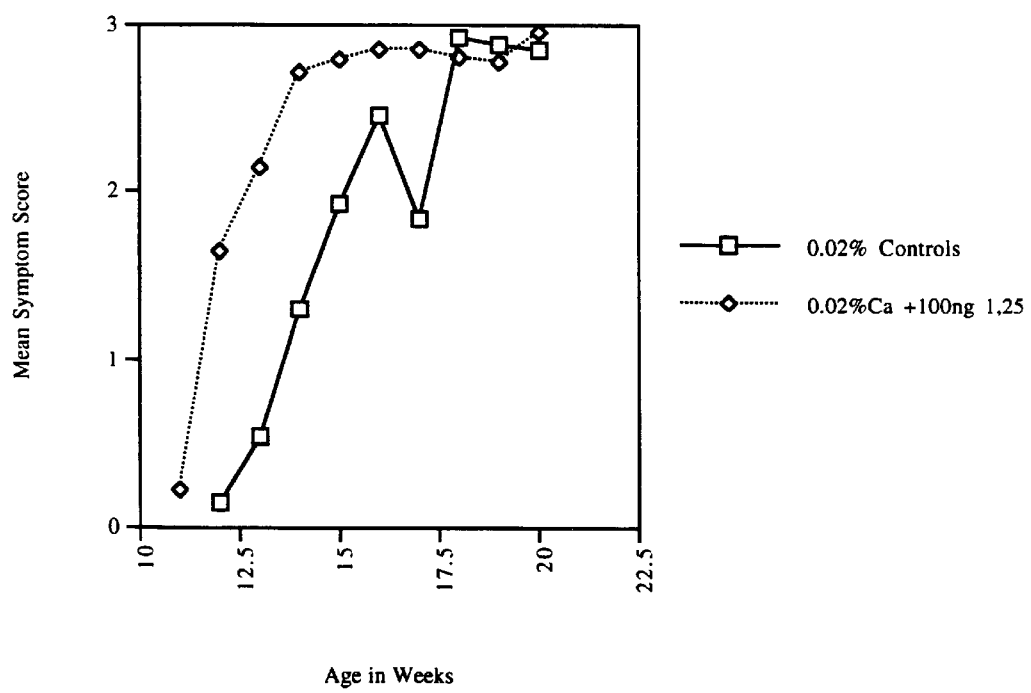

FIG. 3A and B and Tables 3 and 4 disclose data points obtained in this study. At 12 weeks of age the 0.02% Ca+100 ng of $1,25(OH)_2D_3$ group began to show SLE symptoms. It was not until 14 weeks of age that the control (0.02% Ca) mice had the same percentage severity as the mice dosed with $1,25(OH)_2D_3$. Between 18 and 20 weeks of age, about 21.4% of the 0.02% Ca+100 ng $1,25(OH)_2D_3$ mice died. However, none of the controls had reached motality. The experiment was ended at 20 weeks of age.

We conclude that using a low calcium diet and 1,25(OH)$_2$D$_3$ treatment results in disease progression occurring more quickly.

TABLE 3

Summary of Mean symptom scores on 0.02% Ca

| Age in Weeks | 0.02% Ca diet | 0.02% Ca diet + 100 ng 1.25 |
|---|---|---|
| 10 | 0 | 0 |
| 11 | 0 | 0.214 ± 0.410 |
| 12 | 0.142 ± 0.515 | 1.642 ± 0.410 |
| 13 | 0.538 ± 0.747 | 2.14 ± 0.515 |
| 14 | 1.30 ± 1.06 | 2.714 ± 0.45 |
| 15 | 1.923 ± 1.327 | 2.785 ± 0.41 |
| 16 | 2.46 ± 0.603 | 2.85 ± 0.349 |
| 17 | 1.84 ± 1.184 | 2.85 ± 0.349 |
| 18 | 2.92 ± 0.33 | 2.80 ± 0.46 |
| 19 | 2.88 ± 0.62 | 2.77 ± 0.49 |
| 20 | 2.84 ± 0.60 | 2.95 ± 0.33 |

TABLE 4

% Proteinurea scores above 100 mg/dl on 0.02% Ca

| Age in Weeks | 0.02% Ca diet | 0.02% Ca diet + 100 ng 1.25 |
|---|---|---|
| 10 | 0 | 0 |
| 11 | 0 | 0 |
| 12 | 0 | 7.14 |
| 13 | 7.69 | 14.28 |
| 14 | 7.69 | 14.28 |
| 15 | 15.38 | 35.7 |
| 16 | 15.38 | 28.57 |
| 17 | 23.07 | 28.57 |
| 18 | 23.07 | 42.85 |
| 19 | 23.07 | 28.57 |
| 20 | 23.07 | 28.57 |

We claim:

1. A method of treating proteinuria symptoms in an SLE patient comprising orally administering a dose of vitamin D compound effective to reduce or eliminate proteinuria to an SLE patient with a calcium intake level of at least 800 mg/day/160 patient wherein the vitamin D compound is selected from the group of 1,25-dihydroxyvitamin D$_3$, 19-nor-1,25-dihydroxyvitamin D$_2$, 19-nor-21-epi-1,25-dihydroxyvitamin D$_3$, 1,25-dihydroxy-24-homo-22-dehydro-22E vitamin D$_3$, and 19-nor-1,25-dihydroxy-24-homo-22-dehydro-22E-vitamin D$_3$.

2. A method of treating swollen lymph node symptoms in an SLE patient comprising orally administering a dose of vitamin D compound effective to reduce or eliminate swollen lymph nodes to an individual susceptible to SLE patient with a calcium intake level of at least 800 mg/day/160 patient wherein the vitamin D compound is selected from the group of 1,25-dihydroxyvitamin D$_3$, 19-nor-1,25-dihydroxyvitamin D$_2$, 19-nor-21-epi-1,25-dihydroxyvitamin D$_3$, 1,25-dihydroxy-24-homo-22-dehydro-22E vitamin D$_3$, and 19-nor-1,25-dihydroxy-24-homo-22-dehydro-22E-vitamin D$_3$.

3. A method of treating SLE symptoms in individuals susceptible to SLE, comprising orally administering an amount of vitamin D compound effective to prevent symptoms in the individual to an individual susceptible to SLE with a calcium intake level of at least 800 mg/day/160 patient wherein the vitamin D compound is selected from the group of 1,25-dihydroxyvitamin D$_3$, 19-nor-1,25-dihydroxyvitamin D$_2$, 19-nor-21-epi-1,25-dihydroxyvitamin D$_3$, 1,25-dihydroxy-24-homo-22-dehydro-22E vitamin D$_3$, and 19-nor-1,25-dihydroxy-24-homo-22-dehydro-22E-vitamin D$_3$.

4. The method of claim 1 wherein the patient's calcium intake is first adjusted to at least 800 mg/day/160 lb patient, followed by treatment with the vitamin D compound.

5. The method of claim 2 wherein the patient's calcium intake is first adjusted to at least 800 mg/day/160 lb patient, followed by treatment with the vitamin D compound.

6. The method of claim 3 wherein the patient's calcium intake is first adjusted to at least 800 mg/day/160 lb patient, followed by treatment with the vitamin D compound.

7. The method of claim 1 wherein the amount of vitamin D analog administered is between 0.5 and 25 µg per day per 160 pound patient.

8. The method of claim 1 wherein the amount of vitamin D analog administered is between 0.5 and 0.75 µg per day per 160 pound patient.

9. The method of claim 7 wherein the vitamin D analog administered is administered orally and daily.

10. The method of claim 1 wherein the vitamin D analog is co-administered with calcium supplements.

* * * * *